United States Patent [19]

Ungarelli et al.

[11] Patent Number: 4,734,533

[45] Date of Patent: Mar. 29, 1988

[54] PROCESS FOR THE PREPARATION OF (2,2)-PARACYCLOPHANE AND DERIVATIVES THEREOF

[75] Inventors: Raffaele Ungarelli, Novara; Maurizio A. Beretta, Milan; Alessandro Malacrida, Milan; Loris Sogli, Novara, all of Italy

[73] Assignee: Montedison S.p.A., Milan, Italy

[21] Appl. No.: 940,772

[22] Filed: Dec. 12, 1986

[30] Foreign Application Priority Data

Dec. 19, 1985 [IT] Italy ............................ 23299 A/85

[51] Int. Cl.⁴ .................. C07C 17/26; C07C 25/18; C07C 1/32; C07C 13/28
[52] U.S. Cl. ............................. 570/201; 570/141; 585/409
[58] Field of Search ............. 570/143, 190, 201, 141, 570/142; 585/409, 428, 469

[56] References Cited

U.S. PATENT DOCUMENTS

| | | | |
|---|---|---|---|
| 3,198,844 | 8/1965 | Errede et al. | 585/428 |
| 3,349,142 | 10/1967 | Yeh | 570/183 |
| 4,532,369 | 7/1985 | Hartner | 585/469 |

*Primary Examiner*—J. E. Evans
*Attorney, Agent, or Firm*—Stevens, Davis, Miller & Mosher

[57] ABSTRACT

Process for the preparation of (2,2)-paracyclophane or derivatives thereof by the Hofmann elimination of p.-methylbenzyltrimethylammonium hydroxide or derivatives thereof, in an aqueous solution of an alkali metal hydroxide, wherein said elimination is carried out in the presence of a ketone of the formula:

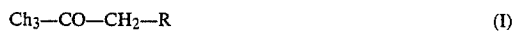

$$Ch_3-CO-CH_2-R \qquad (I)$$

wherein R is hydrogen, a halogen, or an alkyl-carboxylic group.

11 Claims, No Drawings

PROCESS FOR THE PREPARATION OF (2,2)-PARACYCLOPHANE AND DERIVATIVES THEREOF

DESCRIPTION OF THE INVENTION

This invention relates to a process for the preparation of (2,2)-paracyclophane and derivatives thereof having the formula:

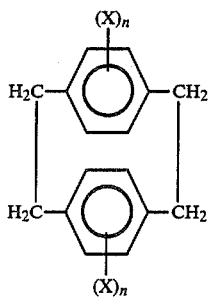
(II)

wherein X may be a halogen, an alkyl, an aralkyl, or a halogenaralkyl radical, and n is zero or an integer from 1 to 4.

More particularly, the invention relates to a process for preparing (2,2)-paracyclophane and its derivatives having the formula (II), starting from a p.-methylbenzyltrimethylammonium hydroxide having formula:

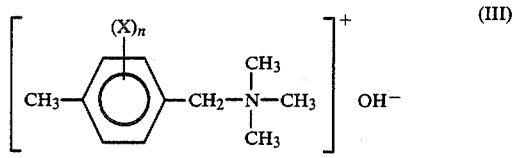
(III)

wherein X and n are the same as defined above, by the Hofmann elimination.

(2,2)-paracyclophane and its derivatives such as dichloro-(2,2)-paracyclophane, tetrachloro-(2,2)-paracyclophane, tetramethyl-(2,2)-paracyclophane, dimethyl-dichloro-(2,2)-paracyclophane, diethyl-(2,2)-paracyclophane, dibromo-(2,2)-paracyclophane, etc., are products well known in the literature and are generally utilized as intermediates in the preparation of the corresponding poly-p.xylylenes. Said polymers, and in particular poly-p.xylylene and its chlorinated derivatives, are advantageously utilized in the form of coating films in the field of the conformal coating obtained by application according to the vacuum vapor deposition technique.

Various processes have been proposed for preparing (2,2)-paracyclophane (II) and its derivatives. However, such known processes are not fully satisfactory and are not suitable for being adopted on an industrial scale, mainly due to the low productivity of the process and to the difficulty in recovering the product from the reaction mixture.

Thus, for example, Organic Syntheses, Coll. Vol. 5, John Wiley & Sons, Inc., New York/London, Sydney/Toronto, 1973, pages 883-886, describes a process for preparing (2,2)-paracyclophane by Hofmann elimination starting from p.-methylbenzyltrimethylammonium hydroxide obtained by reacting the corresponding bromide with silver oxide. The elimination is carried out in the presence of an inert organic solvent (toluene) and a yield of about 10% is attained.

According to European patent aplication No. 108,297, it is possible to increase the reaction yield by carrying out the Hofmann eliomination in an alkaline medium and in the presence of large amounts of dimethyl sulphoxide.

The large volumes and the long reaction times, generally exceeding 50 hours, lead to a low productivity in spite of high yields (about 70%). Furthermore, the recovery of dimethylsulphoxide and the unsatisfactory quality of the resulting product render this process little attractive for industrial-scale utilization.

Generally, in all the known processes for producing (2,2)-paracyclophane, rather large amounts of poly-p.xylylene are formed, which, in the presence of large amounts of organic solvent in the reaction medium, assumes a gelatine-like appearance and is difficult to be filtered off.

In accordance with the present invention, it has now been found that (2,2)-paracyclophane and derivatives thereof having formula (II) may be prepared in a pure form, with high industrial yields, such as higher than 25% by mols, by carrying out the Hofmann elimination of p.-methylbenzyl-trimethylammonium hydroxide, optionally substituted in the nucleus, of formula (III) in an aqueous solution of an alkali metal hydroxide and in the presence of at least a catalytic amount of a ketone having the formula:

$$CH_3-CO-CH_2-R \qquad (I)$$

wherein R is hydrogen, a halogen, such as chlorine or bromine, or an alkyl-carboxylic group containing from 1 to 4 carbon atoms in the alkyl chain.

The p.-methylbenzyltrimethylammonium hydroxide of formula (III), optionally substituted in the nucleus, can be prepared starting from the corresponding halide by means of any conventional process. In practice, p.methylbenzyltrimethylammonium hydroxide, optionally substituted in the nucleus, is preferably formed in situ by the action of the alkali metal hydroxide in the reaction medium. As an alternative, said hydroxide of formula (III) may be prepared separately by eluting an aqueous solution of the corresponding halide through a basic ionic exchange resin column.

Examples of ketones having formula (I) which can be utilized in the process of the present invention area: acetone, chloro-acetone, bromo-acetone, acetyl-acetone, etc.

The ketones of formula (I) may be introduced into the reaction medium as such or they may be generated in situ, starting from their condensation products according to the following reaction:

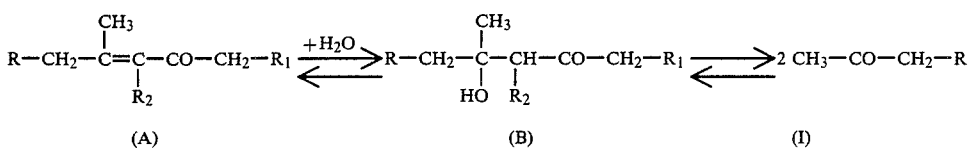

wherein R is the same as defined hereinbefore, and $R_1$ and $R_2$ are the same as R, but at least one of them is hydrogen.

Therefore (A) mesityl oxide or derivatives thereof, or (B) diacetone alcohol or derivatives thereof may be added to the reaction medium a substitutes for the ketones of formula (I), with a similar catalytic effect. Said compounds (A) and (B) are therefore within the scope of the present invention.

The amount of ketones of formula (I) or of compounds of formula (A) or (B) to be added to the reaction medium may vary over a wide range. Amounts between 0.1 and 200% and preferably between 1 and 50% by weight, referred to p.methylbenzyltrimethylammonium hydroxide, optionally substituted in the nucleus, of formula (III), may be used.

According to the invention, the Hofmann elimination is carried out in an alkaline medium consisting or consisting essentially of an aqueous solution of an alkali metal hydroxide having a concentration higher than 20% by weight. As an alkali metal hydroxide, sodium or potassium hydroxide may be used. The aqueous solution is preferably maintained during the Hofmann elimination reaction at a concentration between 25 and 35% by weight.

The Hofmann elimination is carried out at a temperature between 50° and 150° C., preferably between 70° and 125° C., and for a time of 1–40 hours, and preferably for 2–10 hours.

The process of the present invention may be also conducted in the presence of an inert organic solvent such as an aromatic hydrocarbon, toluene, xylene, bezene, etc. being the preferred aromatic hydrocarbons.

At the end of the elimination reaction, the resulting product is separated according to per se known and substantially conventional methods.

The process of this invention permits one to obtain, with industrially acceptable yields—generally higher than 25% by moles and in a few cases even higher than 50% by moles—(2,2)-paracyclophane and its derivatives substituted in the nucleus, with a high degree of purity (above 99.5%) and a high productivity, thanks to the decrease in the reaction volume and the increase in the filtration rate of the polymeric slurry.

The present invention is still further elucidated by the following examples, which however are to be construed as merely illustrative and not limitative of the invention. In the examples, unless otherwise specified, all parts, percentages and ratios are by weight.

EXAMPLE 1 (COMPARATIVE TEST)

Into a 1,000 ml flask equipped with a stirrer, thermometer, and condenser, there were charged:
60 g of an aqueous solution containing 40% by weight of NaOH (0.6 moles); and
62.5 g of an aqueous solution containing 63.9% by weight of p.methylbenzyltrimethylammonium chloride (0.2 moles).

Under continuous stirring, the solution was gradually heated to a temperature of 120° C. The soda concentration was maintained at 30% by weight. The solution was maintained at the boiling temperature over the course of 5 hours.

The resulting (2,2)-paracyclophane was separated from the reaction mass by solubilization in 300 ml of xylene. For this purpose, xylene was added to the reaction mass and the slurry was maintained at full reflux under stirring during 0.5 hours. The reaction mass was filtered at 95° C., the aqueous phase was separated from the organic solution, and this solution was repeatedly washed with water and concentrated to a small volume. The xylene solution was cooled down to 20° C. and the precipitated solid was recovered by filtraton. After washing the solid with acetone and drying, there were obtained 1.08 g of a crystalline white solid, m.p. 283°–285° C., which, on gas-chromatographic analysis, proved to be (2,2)-paracyclophane having a degree of purity of about 99.5%.

EXAMPLES 2–8

Example 1 was repeated, but adding to the aqueous solution of NaOH a compound of the types and in the amounts reported in the following Table I. The amounts of (2,2)-paracyclophane obtained, the relevant melting points, and the reaction yields are indicated in the following Table I:

TABLE I

| Added Compound | | The Obtained Product | | | |
|---|---|---|---|---|---|
| Type | Amount in mols | Amount g. | mols | Molar yield, % | Melting point, °C. |
| Acetone | 0.25 | 10.82 | 0.052 | 52 | 284–287 |
| Acetone | 0.01 | 5.41 | 0.026 | 26 | 284–287 |
| Acetone | 1.00 | 7.70 | 0.037 | 37 | 283–286 |
| Diacetone-alcohol | 0.125 | 11.02 | 0.053 | 53 | 282–286 |
| Mesityl oxide | 0.125 | 9.57 | 0.046 | 46 | 284–288 |
| Acetyl-acetone | 0.25 | 6.45 | 0.031 | 31 | 284–287 |
| Chloroacetone | 0.25 | 5.62 | 0.027 | 27 | 282–288 |

EXAMPLE 9

46.8 g (0.2 moles) of p.-methylbenzyltrimethylammonium chloride, mono-chloro-substituted in the nucleus, 83 g of $H_2O$, 40 g of NaOH, and 18 g of acetone were charged at room temperature into a flask like that of Example 1.

Under stirring, the whole mass was heated at full reflux up to 115° C., whereafter heating was continued over the course of about 3 hours while operating in such manner as to maintain an NaOH concentration of about 32%.

The reaction mixture was treated with 500 ml of n.hexane in hot condition in order to extract the generated dichloro-(2,2)-paracyclophane. This was filtered, the hexane solution was washed with $H_2O$, and the organic solvent was distilled off.

30 g of an oily mass containing dichloro-(2,2)-paracyclophane and by-products were recovered.

The mixture was eluted through a liquid-liquid chromatography column consisting of 350 g of SiO₂, using hexane as an eluent.

From the eluted hexane solution after removal of the solvent, there were obtained 12.6 g (molar yield: about 45%) of a mixture of isomers of the dichlorinated (2,2)-paracyclophane of the formula:

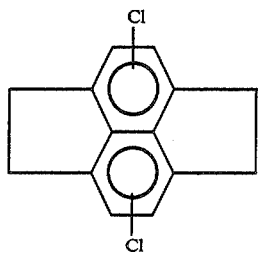

determined by NMR analysis.

The degree of purity of the dichloro-(2,2)-paracyclophane, as determined by gas chromatographic analysis, was higher than 99%.

What is claimed is:

1. A process for preparing (2,2)-paracyclophane and derivatives thereof of the formula:

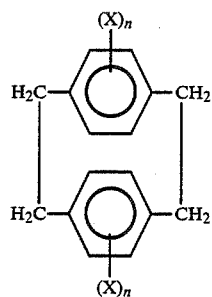 (II)

wherein X is a halogen atom, an alkyl radical, an aralkyl radical, or a halo-aralkyl radical, and n is zero or an integer from 1 to 4, by the Hofmann elimination of p.methylbenzyltrimethylammonium hydroxide or derivatives thereof of the formula:

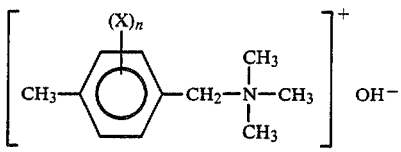 (III)

wherein X and n are the same as defined hereinabove, in an aqueous solution of an alkali metal hydroxide, characterized in that said elimination is carried out at a temperature between 50° and 150° C., and in the presence of at least a catalytic amount of a ketone having the formula:

$$CH_3-CO-CH_2-R \qquad (I)$$

wherein R is hydrogen, halogen, or an alkyl-carboxylic group containing 1 to 4 carbon atoms in the alkyl chain, the ketone concentration being from 0.1 to 200%, based on the p.methylbenzyltrimethylammonium hydroxide or derivatives thereof.

2. The process according to claim 1, wherein the p.methylbenzyltrimethylammonium hydrogen of formula (III) is prepared in situ from the corresponding halide by the action of the alkali metal hydroxide present in the reaction medium.

3. The process according to claim 1 or 2, wherein the ketone of formula (I) is acetone.

4. The process according to claim 1 or 2, wherein the ketone of formula (I) is chloroacetone.

5. The process according to claim 1 or 2, wherein the ketone of formula (I) is acetylacetone.

6. The process according to claim 1 or 2, wherein the ketone of formula (I) is prepared in situ.

7. The process according to claim 6, wherein the ketone of formula (I) is prepared in situ starting from mesityl oxide or a derivative thereof.

8. The process according to claim 6, wherein the ketone of formula (I) is prepared in situ starting from diacetone-alcohol or its derivatives.

9. The process according to claim 1 or 2, wherein the amount of ketone of formula (I), of mesityl oxide or derivatives thereof, or of diacetone alcohol or derivatives thereof, ranges from 1 to 50%, based on p.methylbenzyltrimethylammonium hydroxide.

10. The process according to claim 1 or 2, wherein the concentration of the aqueous solution of an alkali metal hydroxide is maintained, during the Hofmann elimination reaction, at from 25 to 35% by weight.

11. The process according to claim 1 or 2, wherein the Hofmann elimination is carried out at a temperature between 70° and 125° C., over the course of 1–40 hours, and in the presence of an inert organic solvent.

* * * * *